United States Patent [19]

Mikami et al.

[11] Patent Number: 4,965,398
[45] Date of Patent: Oct. 23, 1990

[54] PROCESS FOR PRODUCING OPTICALLY ACTIVE ALPHA-HYDROXYCARBOXYLATES

[75] Inventors: Koichi Mikami, Kanagawa; Masahiro Terada, Tokyo; Takeshi Nakai, Kanagawa; Noboru Sayo, Kanagawa; Hidenori Kumobayashi, Kanagawa, all of Japan

[73] Assignee: Takasago International Corporation, Tokyo, Japan

[21] Appl. No.: 386,480

[22] Filed: Jul. 28, 1989

[30] Foreign Application Priority Data

Jul. 28, 1988 [JP] Japan ................................ 63-189082

[51] Int. Cl.$^5$ ............................................ C07C 69/76
[52] U.S. Cl. ..................................... 560/60; 560/126; 560/183
[58] Field of Search .......................... 560/60, 183, 126

[56] References Cited

U.S. PATENT DOCUMENTS 4,016,196  4/1977  Kogure et al. ........................ 560/60
4,376,866  3/1983  Englaender et al. .................. 560/60
4,820,858  4/1989  Isaacs et al. ............................ 560/60
4,824,972  4/1989  Barner .

FOREIGN PATENT DOCUMENTS 2434244  2/1975  Fed. Rep. of Germany .
1165355  7/1986  Japan .

Primary Examiner—Paul J. Killos
Attorney, Agent, or Firm—Sughrue, Mion, Zinn, Macpeak & Seas

[57] ABSTRACT

A process for preparing an α-hydroxycarboxylate represented by formula (I):

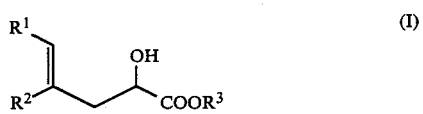

wherein $R^1$ represents a hydrogen atom or a lower alkyl group; $R^2$ represents a lower alkyl group, a phenyl group or a cycloalkyl group, or $R^1$ and $R^2$ are bonded to each other to form a five- to seven-membered cycloalkenyl or bicycloalkenyl ring which may be substituted with a lower alkyl group; and $R^3$ represents a lower alkyl group, which comprises reacting an olefin compound represented by formula (II):

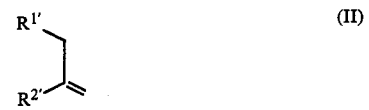

wherein $R^{1'}$ represents a hydrogen atom or a lower alkyl group; and $R^{2'}$ represents a lower alkyl group, a phenyl group or a cycloalkyl group, or $R^{1'}$ and $R^{2'}$ are bonded to each other to form a five- to seven-membered cycloalkyl or bicycloalkyl ring which may be substituted with a lower alkyl group, with a glyoxylate represented by formula (III):

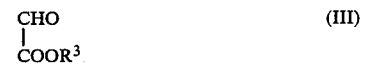

wherein $R^3$ is as defined above,
in the presence of a binaphthol-titanium complex represented by formula (IV):

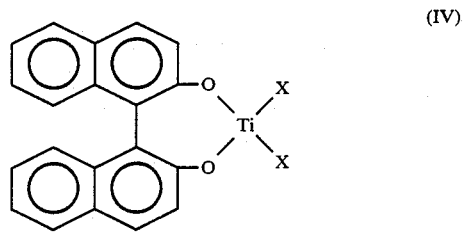

wherein X represents a chlorine atom or bromine atom.

6 Claims, No Drawings

PROCESS FOR PRODUCING OPTICALLY ACTIVE ALPHA-HYDROXYCARBOXYLATES

FIELD OF THE INVENTION

This invention relates to a process for preparing an optically active α-hydroxycarboxylate represented by the following formula (I):

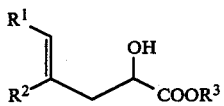

wherein $R^1$ represents a hydrogen atom or a lower alkyl group; $R^2$ represents a lower alkyl group, a phenyl group or a cycloalkyl group, or $R^1$ and $R^2$ are bonded to each other to form a five- to seven-membered cycloalkenyl or bicycloalkenyl ring which may be substituted with a lower alkyl group; and $R^3$ represents a lower alkyl group, which is useful as a intermediate for production of amino acids, medicaments, liquid crystals and others.

BACKGROUND OF THE INVENTION

As a method of preparing the above-described α-hydroxycarboxylate, there has been proposed a process in which 8-phenylmenthyl glyoxylate is reacted with an olefin compound in the presence of a Lewis acid to produce an α-hydroxycarboxylate having a specific absolute configuration [*Tetrahedron*, Vol. 42, pp. 2993–3001 (1986)].

However, the above process for preparing an optically active compound has drawbacks in that depending upon the absolute configuration of the alcohol moiety in the glyoxylate, there can only be obtained a product having either one absolute configuration and in that the Lewis acid should be used in an amount equimolar to the substrate, i.e., glyoxylate.

SUMMARY OF THE INVENTION

Under these circumstances, the present inventors have conducted intensive studies with a view to solving the problems mentioned above. As a result, they have found that the desired α-hydroxycarboxylate having high optical purity can efficiently be obtained by the use of an optically active binaphthol-titanium complex as a catalyst. This invention has been completed based on this novel finding.

It is, therefore, an object of the present invention to provide a process for preparing optically active α-hydroxycarboxylates.

The foregoing and other objects, features and advantages of the present invention will be apparent from the following detailed description and appended claims.

DETAILED DESCRIPTION OF THE INVENTION

According to the present invention, there is provided a process illustrated by the following reaction scheme:

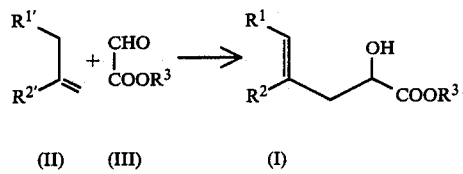

wherein $R^1$, $R^2$ and $R^3$ are as defined hereinbefore; $R^{1'}$ represents a hydrogen atom or a lower alkyl group; and $R^{2'}$ represents a lower alkyl group, a phenyl group or a cycloalkyl group, or $R^{1'}$ and $R^{2'}$ are bonded to each other to form a five- to seven-membered cycloalkyl or bicycloalkyl ring which may be substituted with a lower alkyl group.

That is, the process of the present invention comprises reacting an olefin compound (II) with a glyoxylate (III) in the presence of a binaphtholtitanium complex to produce an optically active α-hydroxycarboxylate (I).

As the olefin compound (II) to be used as a raw material in the present invention, there may be mentioned, for example, 2-methyl-l-propene, 2-methyl-l-butene, 2-methyl-l-pentene, 2-methyl-l-hexene, 2,3-dimethyl-l-butene, 2,3,3-trimethyl-l-butene, 2-ethyl-l-butene, α-methylstyrene, methylenecyclopentane, methylenecyclohexane, methylenecycloheptane, α-fenchene, β-pinene and limonene.

Examples of the glyoxylate (III) to be used as another raw material include methyl glyoxylate, ethyl glyoxylate, isopropyl glyoxylate, and t-butyl glyoxylate. These glyoxylates can be prepared according to the method as described in *Synthesis*, p. 544 (1972).

The optically active binaphthol-titanium complex to be used as a catalyst is one represented by the following formula (IV):

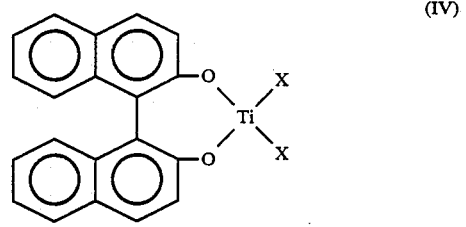

wherein X represents a chlorine or bromine atom.

This binaphthol-titanium complex (IV) can be prepared, for example, by the following method. First, a titanium tetrahalide and titanium tetraisopropoxide are mixed with each other in hexane to give crystals of a diisopropoxydihalogenotitanium, which are then dissolved in toluene. Meanwhile, to methylene chloride is added a powder of Molecular Sieves® 4A in an amount of 0.5 g or more per mmole of the substrate. To this mixture are added the above-prepared toluene solution of diisopropoxydihalogenotitanium and then binaphthol, and the resulting mixture is stirred for about one hour to give the binaphthol-titanium complex (IV).

In practicing the process of the present invention, the olefin compound (II) and the glyoxylate (III) are added to a solution of the binaphthol-titanium complex in an organic solvent, followed by reaction. Though the olefin compound (II) and the glyoxylate (III) are usually used in equimolar amounts, in the case that the olefin compound (II) is in the gaseous state, the former is used in an amount of 10 molar times the latter.

As the organic solvent, there may be employed a halogenated hydrocarbon such as methylene chloride, chloroform, or carbon tetrachloride; an aromatic hydrocarbon such as benzene or toluene; and a aprotic solvent such as tetrahydrofuran, diethyl ether, or dimethoxyethane. An amount of the binaphthol-titanium complex used as a catalyst is generally in the range of from 0.02 to 1 mole, preferably from 0.05 to 0.1 mole, per mole of the substrate, i.e., the glyoxylate (III). A reaction temperature is generally in the range of from $-50°$ C. to $0°$ C., preferably from $-20°$ C. to $-10°$ C. A preferred reaction time is from 10 to 20 hours.

After completion of the reaction, an alkali such as an aqueous sodium hydrogen-carbonate solution is added to the resulting reaction mixture. Subsequently, the reaction mixture is extracted with a solvent such as diethyl ether or ethyl acetate, and the extract is dried. The solvent is distilled off, and the residue is purified by means of, e.g., column chromatography employing silica gel, whereby an intended, optically active α-hydroxycarboxylate can be obtained in a yield as high as 70 to 90%.

As described above, according to the process of the present invention, optically active α-hydroxycarboxylates can efficiently be prepared from olefin compounds and glyoxylates by the use of an optically active binaphthol-titanium complex as a catalyst. Hence, the process of the present invention is industrially of great advantage.

The present invention will be illustrated in more detail with reference to the following Examples, which should not be construed to be limiting the scope of the invention.

In the Examples, the following analytical instruments were employed for respective analyses. $^1$H Nuclear Magnetic Resonance Spectrometry (hereinafter abbreviated as $^1$H NMR):

Type EM390 (90 MHz) (manufactured by Varian Corp.).

Type FX-90Q (90 MHz) (manufactured by JEOL Ltd.).

Measurement of Optical Rotation:

Polarimeter DIP-140 (manufactured by Japan Spectroscopic Co., Ltd.).

Gas Chromatography:

Gas chromatographs GC-8A and GC-9A (manufactured by Shimadzu Corporation).

Column; ULBON-HR ® 20M Silica Capillary ϕ 0.25 mm×25 mm (manufactured by Shinwa Kakoh K.K.).

PEG 20M ϕ 0.25 mm×25 mm (manufactured by Gas-Chro Kogyo K.K.).

High-Performance Liquid Chromatography (HPLC):

Water Model 510 (manufactured by Waters Corp.)

Column; Develosil ® 100-3 (manufactured by Nomura Chemical Co., Ltd.).

Developer; diethyl ether:hexane=1.9, 1 ml/min.

Detector; UV Detector Model 481 (UV254) (manufactured by Waters Corp.).

EXAMPLE 1

Into a 50 ml Schlenk's tube which had been displaced by argon beforehand were introduced 2.98 ml (10 mmoles) of titanium tetraisopropoxide and 5 ml of hexane and then 1.10 ml (10 mmoles) of titanium tetrachloride. The resulting mixture was stirred at room temperature for 10 minutes and allowed to stand at room temperature for 3 hours, whereby a white crystalline precipitate was formed. The solvent was taken out with a syringe, and 5 ml of hexane was added to the residue to effect recrystallization. This procedure was repeated twice. Subsequently, the product was dried under reduced pressure to obtain 3.09 g of a white substance of diisopropoxydichlorotitanium. 43 ml of toluene was added thereto to give a 0.3 N solution.

Into a 25 ml flask was placed 0.5 g of a powder of Molecular Sieves ® 4A (manufactured by Aldrich Corp.), and the air in the flask was thoroughly displaced by argon. Then, 5 ml of methylene chloride was added thereto, and 0.33 ml (0.1 mmole) of the diisopropoxydichlorotitanium solution in toluene as prepared above and 28.6 mg (0.1 mmole) of (R)-binaphthol were further added. The mixture was stirred at room temperature for 1 hour to prepare an (R)-binaphtholdichlorotitanium complex.

The above-obtained solution was cooled to $-70°$ C. in a bath of dry ice and acetone, subsequently 0.56 g (10 mmoles) of 2-methyl-l-propene was bubbled into the cooled solution, and then 88 mg (1 mmole) of methyl glyoxylate was added to the solution. Then, the mixture was allowed to react at $-30°$ C. for 15 hours. Subsequently, 10 ml of an aqueous sodium hydrogencarbonate solution was added to terminate the reaction. The reaction mixture was filtered through Celite and extracted with two 20 ml portions of diethyl ether and two 20 ml portions of ethyl acetate, and the extract was dried over anhydrous magnesium sulfate. Thereafter, the solvents were distilled off, and hexane was added to the residue to crystallize binaphthol. The remaining solution was purified by means of silica gel column chromatography to obtain 0.10 g of methyl (R)-2-hydroxy-4-methyl-4-pentenoate. The yield was 72%.

$^1$H NMR (CDCl$_3$) δ ppm: 1.80 (s, 3H), 2.35 (d, d, J=8.0, 14.0 Hz, 1H), 2.58 (d, d, J=5.0, 14.0 Hz, 1H), 2.70 (b, 1 H), 3.78 (s, 3H), 4.35 (d, d, J=8.0, 5.0 Hz, 1 H), 5.38 (m, 2H).

$[\alpha]_D^{20}$: +7.26° (C=2.46, CHCl$_3$)

The optical purity of the product was measured, after being converted into methyl ether form using silver oxide and methyl iodide, according to proton NMR spectrometry by use of an optically active shift reagent, (+)Eu(DPPM)$_3$ manufactured by Daiichi Pure Chemicals Co., Ltd. [(+)Eu(DPPM)$_3$ means "(+)-tris[di-(perfluoro-2-propoxypropionyl)methanato]europium-(III)"]. As a result, the purity was determined to be 95 %ee.

The absolute structure of the product was examined as follows. The product was first hydrogenated in ethyl acetate using platinum oxide as a catalyst and saponified to give 2-hydroxyisocaproic acid. Then, its optical rotation was measured as follows.

$[\alpha]_D^{20}$: +25.6° (C=1, 1N NaOH):

From the above result, the product was determined to be an (R)-isomer because (−) shows an (S)-isomer.

EXAMPLE 2

A solution of an (S)-binaphthol-dichlorotitanium complex (0.1 mmole) which had been prepared in the same manner as in Example 1 was cooled to $-10°$ C. and there was added thereto 96 mg (1 mmole) of methylenecyclohexane and 88 mg (1 mmole) of methyl glyoxylate, followed by reaction for 8 hours. Then, 10 ml of an aqueous sodium hydrogen carbonate solution was added to terminate the reaction. The reaction mixture was filtered through Celite and extracted with two 20 ml portions of diethyl ether and two 20 ml portions of ethyl acetate, and the extract was dried over anhydrous magnesium sulfate. Thereafter, the solvents were distilled off, and hexane was added to the residue to crystallize binaphthol. The remaining solution was purified by mean of silica gel column chromatography to obtain 0.13 g of methyl (S)-2-hydroxy-3-(1-cyclohexenyl)propanoate. The yield was 73%.

$^1$H NMR (CDCl$_3$) δ ppm: 1.60 (m, 4H), 2.27 (d, d, J=7.5, 13.5 Hz, 1H), 2.40 (b, 1H), 2.48 (d, d, J=5.5, 13.5 Hz, 1H), 3.77 (s, 1 H), 4.30 (d, d, J=5.5, 7.5 Hz, 1H), 5.60 (m, 1H)

$[\alpha]_D^{19}$: +9.72° (C=2.45, CHCl$_3$):

The optical purity of the product was measured in the same manner as in Example 1. That is, the product was converted into methyl ether form and subjected to proton NMR spectrometry employing the same optically active shift reagent. As a result, the purity was determined to be 77 %ee.

EXAMPLE 3

A solution of an (R)-binaphthol-dichlorotitanium complex which had been prepared in the same manner as in Example 1 was cooled to −70° C., into which was bubbled 0.56 g (10 mmoles) of 2-methyl-l-propene, followed by adding thereto 116 mg (1 mmole) of isopropyl glyoxylate. Subsequently, the mixture was reacted at −30° C. for 15 hours. Then, 10 ml of an aqueous sodium hydrogen carbonate solution was added to terminate the reaction. The reaction mixture was filtered through Celite and extracted with two 20 ml portions of diethyl ether and two 20 ml portions of ethyl acetate, and the extract was dried over anhydrous magnesium sulfate. Thereafter, the solvents were distilled off, and the residue was purified by means of silica gel column chromatography to obtain 0.13 g of isopropyl (R)-2-hydroxy-4-methyl-4-pentenoate. The yield was 78%.

$^1$H NMR δ ppm: 1.27 (d, 6.2 Hz, 6H), 1.81 (bs, 3H), 2,35 (d, d, J=8.1, 15.0 Hz, 1H), 2.50 (d, d, J=4.5, 15.0 Hz, 1H), 2.78 (b, 1H), 4.34 (d, d, J=8.1, 4.5 Hz, 1H), 4.9 (m, 1H), 4.95 (m, 1H)

$[\alpha]_D^{20}$: +8.64° (C=1.59, CHCl$_3$).

The optical purity of the product was measured in the same manner as in Example 1. That is, the product was converted into methyl ether form and subjected to proton NMR spectrometry employing the same optically active shift reagent. As a result, the purity was determined to be 65 %ee.

The absolute structure of the product was examined in the same manner as in Example 1. That is, the optical rotation was measured after hydrogenation and saponification. As a result, the product was determined to be an (R)-isomer.

EXAMPLE 4

A solution of an (S)-binaphthol-dichlorotitanium complex which had been prepared in the same manner as in Example 1 was cooled to −30° C. and there was added thereto 0.68 g (5 mmoles) of d-α-fenchene and 0.44 g (5 mmoles) of methyl glyoxylate, followed by reaction for 16 hours. Then, 20 ml of an aqueous sodium hydrogen-carbonate solution was added to terminate the reaction. The reaction mixture was filtered through Celite and extracted with two 20 ml portions of diethyl ether and two 20 ml portions of ethyl acetate, and the extract was dried over anhydrous magnesium sulfate. Thereafter, the solvents were distilled off, and hexane was added to the residue to crystallize binaphthol. The remaining solution was purified by means of silica gel column chromatography to obtained 0.73 g of methyl 3-(7',7'-dimethylbicyclo[2.2.2]-hept-2'-en-1'-yl)-2-hydroxypropanoate. The yield was 65%.

$^1$H NMR δ ppm: 0.90 (s, 3H), 0.99 (s, 3H), 1.16-1.29 (m, 2H), 1.73-2.07 (m, 4H), 2.47-2.52 (m, 1H), 2.76 (d, J=5.8 Hz, 1H), 3.76 (s, 3H), 4.13-4.16 (m, 1H), 5.15-5.23 (m, 1H).

The optical purity of the product was measured by means of HPLC after being converted into the ester form through the reaction with (R)-α-trifluoromethyl-α-emethoxyphenylacetyl chloride in pyridine. As a result, the purity was determined to be 78.6 %ee.

EXAMPLE 5

A solution of an (R)-binaphthol-dichlorotitanium complex which had been prepared in the same manner as in Example 1 was cooled to −30° C. and there was added thereto 84 mg (1 mmole) of 2-ethyl-l-butene and 88 mg (1 mmole) of methyl glyoxylate, followed by reaction for 6 hours. Then, 10 ml of an aqueous sodium hydrogen-carbonate solution was added to terminate the reaction. The reaction mixture was filtered through Celite and extracted with two 20 ml portions of diethyl ether and two 20 ml portions of ethyl acetate, and the extract was dried over anhydrous magnesium sulfate. Thereafter, the solvents were distilled off, and hexane was added to the residue to crystallize binaphthol. The remaining solution wa purified by means of silica gel column chromatography to obtain 117 mg of methyl (R)-2-hydroxy-4-ethyl-2-hexenoate. The yield was 68%.

Upon analysis by gas chromatography, this product was found to be a mixture composed of 89% (E)-isomer and 11% (Z)-isomer.

(E)-isomer:

$^1$H NMR δ ppm: 0.98 (t, J=6.6 Hz, 3H), 1.63 (d, J=7.3 Hz, 3H), 2.11 (q, J=7.8 Hz, 2H), 2.5 (m, 2H), 2.6 (b, 1H), 3.85 (s, 3H), 4.35 (m, 1H), 5.41 (q, J=7.3 Hz, 1H)

(Z)-isomer:

$^1$H NMR δ ppm: 1.00 (t, J=6.6 Hz, 3H), 1.63 (d, J=7.3 Hz, 3H), 2.09 (q, J=7.8 Hz, 2H), 2.5 (m, 2H), 2.6 (b, 1H), 3.85 (s, 3H), 4.35 (m, 1H), 5.55 (q, J=7.3 Hz, 1H).

The optical purity of the product was measured in the same manner as in Example 1. That is, each isomer was converted into a methyl ether form and subjected to proton NMR spectrometry employing the same optically active shift reagent. As a result, the purities of the (E)-isomer and (Z)-isomer were determined to be 72 %ee and 61 %ee, respectively.

EXAMPLE 6

Into a 50-ml Schlenk's tube was introduced 3.68 g (10 mmoles) of titanium tetrabromide, and the air in the tube was displaced by argon. 5 ml of hexane and 2.98 ml (10 mmoles) of titanium tetraisopropoxide were successively added thereto. The mixture was stirred at room temperature for 10 minutes and allowed to stand at room temperature for 3 hours, whereby a white crystalline precipitate was formed. The solvent was taken out with a syringe, and 5 ml of hexane was added to the residue to effect recrystallization. This procedure was repeated twice. Subsequently, the product was dried under reduced pressure to obtain 4.65 g of diisopropoxydibromotitanium as a white substance. 45 ml of toluene was added thereto to give a 0.3N solution.

Into a 25-ml flask was placed 0.5 g of a powder of Molecular Sieves® 4A (manufactured by Aldrich Corp.), and the air in the flask was thoroughly displaced by argon. Then, 5 ml of methylene chloride was added thereto, and 0.16 ml (0.05 mmole) of the diisopropoxydibromotitanium solution in toluene as prepared above and 14.3 mg (0.05 mmole) of (R)-binaphthol were further added. The mixture was stirred at room temperature for 1 hour to prepare an (R)-binaphtholdibromotitanium complex. This solution was cooled to −30° C. in a bath of dry ice and acetone, and subsequently 96 mg (1 mmole) of methylenecyclohexane (manufactured by Aldrich Corp.) and 88 mg (1 mmole) of methyl glyoxylate were added to this cooled solution, followed by reaction for 3 hours. Thereafter, 10 ml of an aqueous sodium hydrogen-carbonate solution was added to terminate the reaction. The reaction mixture was filtered through Celite and extracted with two 20 ml portions of diethyl ether and two 20 ml portions of ethyl acetate, and the extract was dried over anhydrous magnesium sulfate. Then, the solvents were distilled off, and hexane was added to the residue to crystallize binaphthol. The remaining solution was purified by means of silica gel column chromatography to obtain 0.16 g of methyl (S)-2- hydroxy-3-(1-cyclohexenyl)propionate. The yield was 89%.

$[\alpha]_D^{23}$: +13.25° (C=2.12, CHCl$_3$)

$^1$H NMR (CDCl$_3$) δ ppm: 1.60 (m, 4H), 2.27 (d, d, J=7.5, 13.5 Hz, 1H), 2.40 (b, 1H), 2.48 (d, d, J=5.5, 13.5 Hz, 1H), 3.77 (s, 1H), 4.30 (d, d, J=5.5, 7.5 Hz, 1H), 5.60 (m, 1H)

The optical purity of the product was measured in the same manner as in Example 1. That is, the product was converted into the methyl ether form and subjected to proton NMR spectrometry employing the same optically active shift reagent. As a result, the purity was determined to be 86 %ee.

EXAMPLE 7

A solution of an (R)-binaphthol-dichlorotitanium complex which had been prepared in the same manner as in Example 1 was cooled to −30° C. and added with 118 mg (1 mmole) of α-methylstyrene and 88 mg (1 mmole) of methyl glyoxylate, followed by reaction for 15 hours. Then, 10 ml of an aqueous sodium hydrogen-carbonate solution was added to terminate the reaction. The reaction mixture was filtered through Celite and extracted with two 20 ml portions of diethyl ether and two 20 ml portions of ethyl acetate, and the extract was dried over anhydrous magnesium sulfate. Thereafter, the solvents were distilled off, and hexane was added to the residue to crystallize binaphthol. The remaining solution was purified by means of silica gel column chromatography to obtain 200 mg of methyl (R)-2-hydroxy-4-phenyl-4-pentenoate. The yield was 97%.

$[\alpha]_D^{23}$: +30.55° (C=4.83, CHCl$_3$).

$^1$H NMR (CDCl$_3$) δ ppm: 2.76 (bs, 1H), 2.88 (d, d, J=8.1, 13.5 Hz, 1H), 3.13 (d, d, J=4.5, 13.5 Hz, 1H), 3.68 (s, 3H), 4.33 (m, 1H), 5.28 (bs, 1H), 5.48 (bs, 1H), 7.45 (m, 5H).

The optical purity of the product was measured in the same manner as in Example 1. That is, the product was converted into a methyl ether form and subjected to proton NMR spectrometry employing the same optically active shift reagent. As a result, the purity was determined to be 97 %ee.

EXAMPLE 8

A solution of an (R)-binaphthol-dibromotitanium complex which had been prepared in the same manner as in Example 6 was cooled to −30° C. and added with 82 mg (1 mmole) of methylenecyclopentane (manufactured by Aldrich Corp.) and 88 mg (1 mmole) of methyl glyoxylate, followed by reaction for 3 hours. Then, 10 ml of an aqueous sodium hydrogen-carbonate solution was added to terminate the reaction. The reaction mixture was filtered through Celite and extracted with two 20 ml portions of diethyl ether and two 20 ml portions of ethyl acetate, and the extract was dried over anhydrous magnesium sulfate. Thereafter, the solvents were distilled off, and hexane was added to the residue to crystallize binaphthol. The remaining solution was purified by means of silica gel column chromatography to obtain 156 mg of methyl (R)-2-hydroxy-3-(1-cyclopentenyl)propionate. The yield was 92%.

$[\alpha]_D^{23}$: +7.55° (C=4.20, CHCl$_3$)

$^1$H NMR δ ppm: 1.90 (m, 2H), 2.30 (m, 4H), 2.58 (m, 2H), 2.73 (m, 2H), 3.85 (s, 3H), 4.40 (m, 1H), 5.62 (m, 1H)

The optical purity of the product was measured in the same manner as in Example 1. That is, the product was converted into methyl ether form and subjected to proton NMR spectrometry employing the same optically active shift reagent. As a result, the purity was determined to be 89 %ee.

While the invention has been described in detail and with reference to specific embodiments thereof, it will be apparent to one skilled in the art that various changes and modifications can be made therein without departing from the spirit and scope thereof.

What is claimed is:

1. A process for preparing an α-hydroxycarboxylate represented by formula (I):

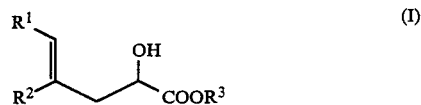

wherein R$^1$ represents a hydrogen atom or a lower alkyl group; R$^2$ represents a lower alkyl group, a phenyl group or a cycloalkyl group, or R$^1$ and R$^2$ are bonded to each other to form a five- to seven-membered cycloalkenyl or bicycloalkenyl ring which may be substituted with a lower alkyl group; and R$^3$ represents a lower alkyl group, which comprises reacting an olefin compound represented by formula (II):

wherein R$^{1'}$ represents a hydrogen atom or a lower alkyl group; and R$^{2'}$ represents a lower alkyl group, a phenyl group or a cycloalkyl group, or R$^{1'}$ and R$^{2'}$ are bonded to each other to form a five- to seven-membered cycloalkyl or bicycloalkyl ring which may be substituted with a lower alkyl group, with a glyoxylate represented by formula (III):

(III)

wherein $R^3$ is as defined above, in the presence of a binaphthol-titanium complex represented by formula (IV):

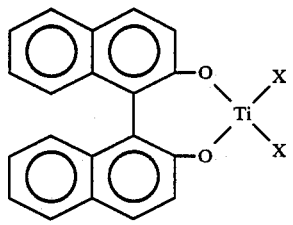

wherein X represents a chlorine atom or bromine atom.

2. A process as in claim 1, wherein said olefin compound represented by formula (II) is 2-methyl-l-propene, 2-methyl-l-butene, 2-methyl-l-pentene, 2-methyl-l-hexene, 2,3-dimethyl-l-butene, 2,3,3-trimethyl-l-butene, 2-ethyl-l-butene, α-methylstyrene, methylenecyclopentane, methylenecyclohexane, methylenecycloheptane, α-fenchene, β-pinene, or limonene.

3. A process as in claim 1, wherein said glyoxylate represented by formula (III) is methyl glyoxylate, ethyl glyoxylate, isopropyl glyoxylate, or t-butyl glyoxylate.

4. A process as in claim 1, wherein said binaphthol-titanium complex represented by formula (IV) is used in the range of from 0.02 to 1 mole per mole of said glyoxylate represented by formula (III).

5. A process as in claim 1, wherein the reaction of said olefin compound represented by formula (II) and said glyoxylate represented by formula (III) is carried out at a temperature in the range of from −50° C. to 0° C.

6. A process as in claim 1, wherein the reaction of said olefin compound represented by formula (II) and said glyoxylate represented by formula (III) is carried out for from 10 to 20 hours.

* * * * *